US011958883B2

(12) United States Patent
Ouh et al.

(10) Patent No.: US 11,958,883 B2
(45) Date of Patent: Apr. 16, 2024

(54) RECOMBINANT CANINE PARVOVIRUS 2a VP2 AND 2b VP2 ANTIGEN PROTEIN, AND USE THEREOF

(71) Applicants: REPUBLIC OF KOREA(ANIMAL AND PLANT QUARANTINE AGENCY), Gyeongsangbuk-do (KR); BIOAPPLICATIONS INC., Gyeongsangbuk-do (KR)

(72) Inventors: In-Ohk Ouh, Gyeongsangbuk-do (KR); Jae-Young Song, Gyeonggi-do (KR); Ju-Yeon Lee, Gyeongsangbuk-do (KR); Soo Dong Cho, Gyeonggi-do (KR); Jienny Lee, Gyeonggi-do (KR); Yongjik Lee, Gyeongsangbuk-do (KR)

(73) Assignees: REPUBLIC OF KOREA(ANIMAL AND PLANT QUARANTINE AGENCY), Gyeongsangbuk-do (KR); BIOAPPLICATIONS INC., Gyeongsangbuk-do (KR)

( * ) Notice: Subject to any disclaimer, the term of this patent is extended or adjusted under 35 U.S.C. 154(b) by 263 days.

(21) Appl. No.: 17/604,641

(22) PCT Filed: Apr. 17, 2020

(86) PCT No.: PCT/KR2020/005163
§ 371 (c)(1),
(2) Date: Oct. 18, 2021

(87) PCT Pub. No.: WO2020/213987
PCT Pub. Date: Oct. 22, 2020

(65) Prior Publication Data

US 2022/0194991 A1 Jun. 23, 2022

(30) Foreign Application Priority Data

Apr. 19, 2019 (KR) ........................ 10-2019-0046350

(51) Int. Cl.

| | |
|---|---|
| ***C12N 15/82*** | (2006.01) |
| ***A61K 39/23*** | (2006.01) |
| ***C07K 14/005*** | (2006.01) |
| ***C12N 7/00*** | (2006.01) |

(52) U.S. Cl.
CPC ............ *C07K 14/005* (2013.01); *A61K 39/23* (2013.01); *C12N 7/00* (2013.01); *C12N 15/8258* (2013.01); *C12N 2750/14322* (2013.01); *C12N 2750/14334* (2013.01)

(58) Field of Classification Search
CPC ................................................. C12N 15/8258
See application file for complete search history.

(56) References Cited

U.S. PATENT DOCUMENTS 6,187,759 B1 2/2001 Tarpey et al.
2004/0093644 A1 * 5/2004 Rymerson .......... C12N 15/8258 424/751

FOREIGN PATENT DOCUMENTS

WO WO 2020/099922 A1 * 5/2020

OTHER PUBLICATIONS

Lonsdale et al Plant Cell Reports vol. 17, pp. 396-399 (Year: 1998).*
Xiong et al Virologica Sinica vol. 23, No. 3, pp. 203-210 (Year: 2008).*
International Search Report from corresponding PCT Application No. PCT/KR2020/005163, dated Aug. 11, 2020.
Notice of Allowance from corresponding Korean Patent Application No. 10-2019-0046350, dated May 7, 2020.
Xiong, N., et al.; "Isolation and identification of canine parvovirus serotype 2a and its VP2 protein expression in transgenic tobacco", Virologica Sinica, 2008, vol. 23, No. 3, pp. 203-210.
NCBI. GenBank accession No. MH545963.1. Canine parvovirns 2a strain TN/CPV2a/20I8, complete genome. (Oct. 8, 2018).
NCBI. GenBank accession No. KP893077. I. Canine parvovims isolate QIACPVI403 VP2, gene, compleie eds. (Jun. 30, 2015).
Song, Jae-yeong et al. Development of Plant-Derived Edible Vaccine against Canine Parvovirns. Final Report of Research Project for Veterinary Science Technology Development, May 20, 2013.

* cited by examiner

*Primary Examiner* — David H Kruse
(74) *Attorney, Agent, or Firm* — Harness, Dickey & Pierce, P.L.C.

(57) ABSTRACT

The present invention provides a recombinant expression vector comprising a gene encoding canine parvovirus 2a VP2 or 2b VP2 protein, a recombinant plant into which the vector is transformed, a vaccine composition against canine parvovirus, comprising canine parvovirus 2a VP2 or 2b VP2 protein obtained from the recombinant plant, and a composition for diagnosing canine parvovirus. When the recombinant plant of the present invention is used, canine parvovirus 2a VP2 or 2b VP2 antigen protein can be rapidly produced with high efficiency. Since the composition for diagnosing canine parvovirus according to the present invention uses a recombinant antigen protein, there is no possibility of contamination due to live virus handling, and thus the composition is safe, and the presence or absence of canine parvovirus infection can be rapidly diagnosed from a large amount of samples.

2 Claims, 3 Drawing Sheets

Specification includes a Sequence Listing.

S: Supernatant

P: Precipitate

| Recombinant Protein | HA titer |
|---|---|
| Recombinant CPV 2a VP2 protein | $2^{15}$ |

| Recombinant Protein | HA titer |
|---|---|
| Recombinant CPV 2b VP2 protein | $2^{20}$ |

| Recombinant Protein | HI titer |
|---|---|
| Recombinant CPV 2a VP2 protein | $2^6$ |

| Recombinant Protein | HA titer |
|---|---|
| Recombinant CPV 2b VP2 protein | $2^8$ |

```
                              SEQUENCE LISTING


<160> NUMBER OF SEQ ID NOS: 6

<210> SEQ ID NO 1
<211> LENGTH: 231
<212> TYPE: DNA
<213> ORGANISM: Artificial Sequence
<220> FEATURE:
<223> OTHER INFORMATION: DNA sequence of Rubisco transit peptide

<400> SEQUENCE: 1

atggcttcct ctatgctctc ttccgctact atggttgcct ctccggctca ggccactatg      60

gtcgctcctt tcaacggact taagtcctcc gctgccttcc cagccacccg caaggctaac     120

aacgacacta cttccatcac aagcaacggc ggaagagtta actgcatgca ggtgtggcct     180

ccgattggaa agaagaagtt tgagactctc tcttaccttc ctgaccttac c              231


<210> SEQ ID NO 2
<211> LENGTH: 18
<212> TYPE: DNA
<213> ORGANISM: Artificial Sequence
<220> FEATURE:
<223> OTHER INFORMATION: DNA sequence of 6XHis

<400> SEQUENCE: 2

caccaccatc accaccat                                                    18


<210> SEQ ID NO 3
<211> LENGTH: 1752
<212> TYPE: DNA
<213> ORGANISM: Artificial Sequence
<220> FEATURE:
<223> OTHER INFORMATION: CPV-2a Nicotiana benthamiana optimized sequence

<400> SEQUENCE: 3

atgtctgatg gtgctgtcca acctgatggc ggtcagccag ccgtgcgaaa cgaaagggct      60

actgggtctg gcaacggctc cggaggaggg ggagggggag gcagcggcgg agtggggata     120

agtactggca ccttcaataa ccaaacagag tttaaatttc tcgaaaacgg gtgggtcgag     180

attacggcca actcatcaag actcgttcac ttaaatatgc cagagtcaga aaattacaga     240

cgtgtcgtag tcaataactt agacaagacg gccgtcaacg gaaacatggc tctggatgac     300

acacatgccc agattgttac gccgtggtca ctcgtggacg caaacgcatg ggtgtgtgg     360

ttcaacccag gtgactggca gcttatcgtt aacacaatgt ctgagttgca cttggtgtct     420

ttcgagcagg agatttttaa cgtggtgttg aaaactgtca gcgagagcgc cacgcagcca     480

cccacgaagg tatataataa tgacctgacc gccagtctga tggtcgctct ggattctaac     540
```

```
aatacaatgc catttacgcc cgctgcaatg aggagcgaga cgctcgggtt ctacccctgg    600
aaaccgacaa tacccacacc ttggagatac tactttcagt gggatagaac tctgatccca    660
agccatacag ggacaagcgg gacgccaacg aacatatacc acggcactga cccggacgat    720
gtccaatttt acacgataga aaactccgtg cccgtccatt tgctccgaac cggcgatgag    780
tttgctactg gaacgtttta ctttgattgt aagccatgta ggctgacgca cacatggcaa    840
acgaataggg cccttgggtt acccccgttc ttaaatagtc ttccgcaagc cgagggtggg    900
acaaattttg gctatatcgg cgttcaacag gataagaggc gaggggtaac gcaaatgggt    960
aacacgaata taatcacgga ggccaccatc atgcgaccag ctgaagtcgg atacagcgca   1020
ccatattatt ctttcgaagc cagtacacag ggccccttca aaactccaat tgctgctggt   1080
cgaggcggcg cccagactga tgaaaaccaa gccgctgatg gcgacccacg atatgctttt   1140
ggtagacagc acgggcaaaa gacaacgacc accggggaga ccccggagcg ttttacttac   1200
atagcacacc aagatacagg aagatatccg gagggggatt ggattcagaa tataaacttc   1260
aacctcccag ttaccaacga taacgtactt ctcccaacgg acccaatcgg cggaaaagca   1320
gggattaatt atactaacat attcaatact tacggcccat taaccgcttt gaataacgtg   1380
ccgccggttt accctaatgg tcagatttgg gataaagaat ttgacaccga tttgaagcct   1440
cgattacatg tcaatgctcc ttttgtatgt caaaataact gtcccggtca attgttcgta   1500
aaagttgccc ccaatctgac caacgagtat gacccggatg caagtgcaaa catgagtaga   1560
atagtcacgt acagtgactt ctggtggaaa ggcaagttag ttttcaaagc caaattaagg   1620
gcatcacaca cgtggaatcc gatccagcaa atgagtataa acgttgacaa tcagtttaat   1680
tatgtccctt ctaatatcgg aggtatgaaa atagtatacg aaaaatccca acttgctcct   1740
cgaaagcttt ac                                                       1752
```

<210> SEQ ID NO 4
<211> LENGTH: 1752
<212> TYPE: DNA
<213> ORGANISM: Artificial Sequence
<220> FEATURE:
<223> OTHER INFORMATION: CPV-2b Nicotiana benthamiana optimized sequence

<400> SEQUENCE: 4

```
atgagtgatg gggccgtgca accggatggg ggccaaccgg cagtgagaaa cgaaagagca     60
accggctctg gaaatggcag cgggggcgga ggcggaggcg gtagcggggg agtagggatc    120
tctactggaa ctttcaataa ccagacggaa tttaaatttt tggaaaatgg atgggtggaa    180
atcactgcta attcatctcg tttagtccac ctgaacatgc ccgaaagtga aaactataga    240
agagttgtag tcaataacct ggataagacc gcagtgaatg gcaatatggc cttggacgac    300
acacacgctc aaatcgttac tccctggtcc cttgtggacg ctaatgcatg gggcgtctgg    360
tttaatcccg gtgattggca gctcatcgtc aacacgatgt ccgagcttca cctcgtttct    420
ttcgaacagg aaatcttcaa cgttgtgctc aaaactgtct ccgagtctgc aactcaaccg    480
cccacaaagg tgtacaataa tgacttaact gccagtttaa tggtcgccct ggatagtaat    540
aacacaatgc cgttcacccc agcagctatg cgttccgaga ctttaggttt ttatccctgg    600
aaaccgacca ttccgactcc ctggagatac tattttcagt gggataggac tttgatccca    660
agccacacgg ggacctctgg gacacctaca aacatctacc atgggaccga ccctgacgac    720
gtacaatttt atacaattga gaacagcgtt cctgtacacc ttttgaaaac gggggacgag    780
```

-continued

```
tttgctacgg gcacgttcta ctttgactgc aaaccgtgtc gattgacgca cacctggcaa    840

actaataggg ctttgggtct cccaccgttt ctcaactccc ttccacaggc tgagggcggc    900

acaaacttcg gttacattgg cgtacagcag gacaagagga gaggggttac gcagatgggc    960

aatacaaaca taataaccga agctacaatc atgcgaccgg ccgaagtcgg ttatagtgcc   1020

ccctactact cttttgaagc aagtactcaa gggccattta aaacaccgat agctgctggg   1080

agaggaggcg ctcaaactga tgaaaaccaa gccgcagatg gagatccacg atacgcattc   1140

ggtcgtcagc acggccaaaa gactacaaca accggtgaaa ccccggaaag atttacttat   1200

atagctcacc aggacaccgg tcgataccct gaaggagact ggatacaaaa tatcaacttt   1260

aacttgccgg tcaccgacga taacgtcctg cttccaacag atcccattgg gggtaaggct   1320

ggtatcaatt atacaaatat tttcaacacc tacggcccgc ttacagcact taataatgta   1380

cctcctgtgt accctaacgg gcaaatatgg gataaggaat ttgacactga tctcaagcca   1440

aggctgcacg ttaatgcacc ctttgtatgt cagaacaact gtccggggca attgtttgtc   1500

aaggttgcac ctaatttaac aaacgaatat gatccagacg cctcagcaaa tatgtcccgt   1560

attgtcacat acagcgactt ttggtggaag ggcaaattag tcttcaaggc taaactgcgt   1620

gctagccata catggaatcc gattcaacag atgtctatca atgtcgacaa ccagtttaac   1680

tatgtgccta gcaacatagg gggaatgaaa attgtgtatg aaaaatctca actggctcca   1740

cgtaagctct ac                                                       1752
```

<210> SEQ ID NO 5
<211> LENGTH: 1752
<212> TYPE: DNA
<213> ORGANISM: Artificial Sequence
<220> FEATURE:
<223> OTHER INFORMATION: CPV 2a original

<400> SEQUENCE: 5

```
atgagtgatg gagcagttca accagacggt ggtcagcctg ctgtcagaaa tgaaagagct     60

acaggatctg ggaacgggtc tggaggcggg ggtggtggtg gttctggggg tgtggggatt    120

tctacgggta ctttcaataa tcagacggaa tttaaatttt tggaaaacgg atgggtggaa    180

atcacagcaa actcaagcag acttgtacat ttaaatatgc cagaaagtga aaattataga    240

agagtggttg taaataattt ggataaaact gcagttaacg gaaacatggc tttagatgat    300

acccatgcac aaattgtaac accttggtca ttggttgatg caaatgcttg gggagtttgg    360

tttaatccag gagattggca actaattgtt aatactatga gtgagttgca tttagttagt    420

tttgaacaag agatttttaa tgttgtttta aagactgttt cagaatctgc tactcagcca    480

ccaactaaag tttataataa tgatttaact gcatcattaa tggttgcatt agatagtaat    540

aatactatgc catttactcc agcagctatg agatctgaga cattgggttt ttatccatgg    600

aaaccaacca taccaactcc atggagatat tattttcaat gggatagaac attaatacca    660

tctcatactg gaactagtgg cacaccaaca aatatatacc atggtacaga tccagatgat    720

gttcaatttt acactattga aaattctgtg ccagtacact tactaagaac aggtgatgaa    780

tttgctacag gaacatttta ttttgattgt aaaccatgta gactaacaca cacatggcaa    840

acaaacagag cattgggctt accaccattt ctaaattctt tgcctcaagc tgaaggaggt    900

actaactttg gttatatagg agttcaacaa gataaaagac gtggtgtaac tcaaatggga    960

aatacaaaca ttattactga agctactatt atgagaccag ctgaggttgg ttatagtgca   1020

ccatattatt cttttgaggc gtctacacaa gggccattta aaacacctat tgcagcagga   1080
```

```
cgggggggag cgcaaacaga tgaaaatcaa gcagcagatg gtgatccaag atatgcattt   1140
ggtagacaac atggtcaaaa aactaccaca acaggagaaa cacctgagag atttacatat   1200
atagcacatc aagatacagg aagatatcca gaaggagatt ggattcaaaa tattaacttt   1260
aaccttcctg taacaaatga taatgtattg ctaccaacag atccaattgg aggtaaagca   1320
ggaattaact atactaatat atttaatact tatggtcctt taactgcatt aaataatgta   1380
ccaccagttt atccaaatgg tcaaatttgg gataaagaat ttgatactga cttaaaacca   1440
agacttcatg taaatgcacc atttgtttgt caaaataatt gtcctggtca attatttgta   1500
aaagttgcgc ctaatttaac aaatgaatat gatcctgatg catctgctaa tatgtcaaga   1560
attgtaactt actcagattt ttggtggaaa ggtaaattag tatttaaagc taaactaaga   1620
gcctctcata cttggaatcc aattcaacaa atgagtatta atgtagataa ccaatttaac   1680
tatgtaccaa gtaatattgg aggtatgaaa attgtatatg aaaaatctca actagcacct   1740
agaaaattat ac                                                         1752
```

<210> SEQ ID NO 6
<211> LENGTH: 1752
<212> TYPE: DNA
<213> ORGANISM: Artificial Sequence
<220> FEATURE:
<223> OTHER INFORMATION: CPV 2b original

<400> SEQUENCE: 6

```
atgagtgatg gagcagttca accagacggt ggtcagcctg ctgtcagaaa tgaaagagct     60
acaggatctg ggaacgggtc tggaggcggg ggtggtggtg gttctggggg tgtggggatt    120
tctacgggta ctttcaataa tcagacggaa tttaaatttt tggaaaacgg atgggtggaa    180
atcacagcaa actcaagcag acttgtacat ttaaatatgc cagaaagtga aaattataga    240
agagtggttg taaataattt ggataaaact gcagttaacg gaaacatggc tttagatgat    300
acccatgcac aaattgtaac accttggtca ttggttgatg caaatgcttg gggagtttgg    360
tttaatccag gagattggca actaattgtt aatactatga gtgagttgca tttagttagt    420
tttgaacaag aaatttttaa tgttgtttta aagactgttt cagaatctgc tactcagcca    480
ccaactaaag tttataataa tgatttaact gcatcattga tggttgcatt agatagtaat    540
aatactatgc catttactcc agcagctatg agatctgaga cattgggttt ttatccatgg    600
aaaccaacca taccaactcc atggagatat tattttcaat gggatagaac attaatacca    660
tctcatactg gaactagtgg cacaccaaca aatatatacc atggtacaga tccagatgat    720
gttcaatttt acactattga aaattctgtg ccagtacact tactaaaaac aggtgatgaa    780
tttgctacag gaacatttta ttttgattgt aaaccatgta gactaacaca cacatggcaa    840
acaaatagag cattgggctt accaccattt ctaaattctt tgcctcaagc tgaaggaggt    900
actaactttg gttatatagg agttcaacaa gataaaagac gtggtgtaac tcaaatggga    960
aatacaaaca ttattactga agctactatt atgagaccag ctgaggttgg ttatagtgca   1020
ccatattatt cttttgaggc gtctacacaa gggccattta aaacacctat tgcagcagga   1080
cgggggggag cgcaaacaga tgaaaatcaa gcagcagatg gtgatccaag atatgcgttt   1140
ggtagacaac atggtcaaaa aactaccaca acaggagaaa cacctgagag atttacatat   1200
atagcacatc aagatacagg aagatatcca gaaggagatt ggattcagaa tattaacttt   1260
aaccttcctg taacagatga taatgtattg ctaccaacag atccaattgg aggtaaagca   1320
```

-continued

```
ggaattaact atactaatat atttaatact tatggtcctt taactgcatt aaataatgta   1380

ccaccagttt atccaaatgg tcaaatttgg gataaagaat ttgatactga cttaaaacca   1440

agacttcatg taaatgcacc atttgtttgt caaaataatt gtcctggtca attatttgta   1500

aaagttgcgc ctaatttaac aaatgaatat gatcctgatg catctgctaa tatgtcaaga   1560

attgtaactt actcagattt ttggtggaaa ggtaaattag tatttaaagc taaactaaga   1620

gcctctcata cttggaatcc aattcaacaa atgagtatta atgtagataa ccaatttaac   1680

tatgtaccaa gtaatattgg aggtatgaaa attgtatatg aaaaatctca actagcacct   1740

agaaaattat ac                                                       1752
```

RECOMBINANT CANINE PARVOVIRUS 2a VP2 AND 2b VP2 ANTIGEN PROTEIN, AND USE THEREOF

CROSS-REFERENCE TO RELATED APPLICATIONS

This application is a national phase application of PCT Application No. PCT/KR2020/005163, filed on Apr. 17, 2020, which claims priority to Korean Patent Application No. 10-2019-0046350, filed on Apr. 19, 2019. The entire disclosures of the applications identified in this paragraph are incorporated herein by references.

TECHNICAL FIELD

The present disclosure relates to canine parvovirus 2a VP2 and 2b VP2 antigen proteins and a use thereof.

The present disclosure was made with the support of the Ministry of Agriculture, Food, and Rural Affairs, Republic of Korea, under Project No. 1545016907, which was supervised by the Animal and Plant Quarantine Agency, Agriculture and Forestry in the research project named "Development of High-Quality Purified Vaccine for Companion Animals by Using Plant Expression System" under management of the Korea Institute of Planning and Evaluation for Technology in Food for the project named "Support Project for Technology Commercialization", from Jan. 1, 2018 to Dec. 31, 2018.

BACKGROUND ART

After its first recognition in 1987, canine parvovirus (CPV) infection symptoms were spread worldwide. In South Korea, the outbreak of canine parvovirus (CPV) infection symptoms was first identified in the 1980s in Gyeonggi-do and then spread nationwide. There are two main clinical or pathological types of canine parvovirus: cardiac form and intestinal form, the cardiac form being found in puppies 3-8 weeks of age and the intestinal form found in dogs after ablactation. Dogs infected with the intestinal form mainly undergo severe vomiting, bloody diarrhea, dehydration, and a low white blood cell count, with a high mortality rate.

Canine parvovirus symptoms are similar in clinical symptoms and pathological opinions to feline panleukopenia (FPL) and are known to be effectively treated by symptomatic therapy. The cardiac form is characterized by nonsuppurative myocarditis at and around the left ventricle and generally progresses to acute symptoms with high mortality rate and poor prognosis.

Parvovirus is spread from dog to dog by oral contact with their diarrhea feces. For acute types, a tremendous amount of viruses is released through feces for 1-2 weeks after infection. Released viruses survive ordinary living environments for several months, with their pathogenicity maintained.

CPV is referred to as "CPV-2" for discrimination from canine minute virus (CMV or CPV-1). CPV-2 is generally considered to be a genetic variant of feline panleukopenia virus (FPV) or mink enteric virus (MEV) and is in genetically and antigenically very close relationship with parvoviruses infecting minks, foxes, raccoons, and other carnivores. The CPV capsid contains a single-stranded DNA genome of about 5200 bases with only two open reading frames, although at least four proteins are encoded due to alternative mRNA splicing.

Parvovirus capsid is made up of two viral proteins (VP), VP1 and VP2, with VP2 being the major immunogenic parvovirus capsid protein. A genetic variant of the original CPV isolate was identified and named CPV type 2a. Yet another variant, type 2b, was named. Recently, type 2c has been identified.

The best strategy for preventing canine parvovirus infection is vaccination. Attenuated canine parvovirus vaccines are ideal because they can last effective immunity for a long period of time, but care must be taken because the efficacy of the vaccine can be dropped with the influence of maternal antibodies.

Currently, the canine parvovirus vaccine mainly used in Korea, which is a kind of recombinant attenuated live vaccines, is commercially available in the form of a five mixed vaccine including canine distemper, infectious canine hepatitis, parainfluenza, and leptospira.

SUMMARY

Technical Problem

Leading to the present disclosure, intensive and thorough research, conducted by the present inventors, into the development of a recombinant canine parvovirus antigen protein as an antigenic protein with excellent antigenicity and immunogenicity, succeeded in codon optimization and synthesis of canine parvovirus 2a VP2 and 2b VP2 genes and resulted in the finding that canine parvovirus 2a VP2 and 2b VP2 antigen proteins obtained from recombinant plants transformed with recombinant vectors comprising the genes have high stability and immunogenicity.

Therefore, an aspect of the present disclosure is to provide a recombinant canine parvovirus 2a VP2 or 2b VP2 protein expressing vector.

Another aspect of the present disclosure is to provide a transgenic recombinant plant expressing a recombinant canine parvovirus 2a VP2 or 2b VP2 protein.

Another aspect of the present disclosure is to provide a composition for canine parvovirus vaccination.

Another aspect of the present disclosure is to provide a composition for diagnosis of canine parvovirus infection.

Another aspect of the present disclosure is to provide a method for providing information necessary for diagnosis of canine parvovirus infection.

Solution to Problem

According to an aspect thereof, the present disclosure provides a recombinant expression vector comprising a gene encoding a canine parvovirus 2a VP2 or 2b VP2 protein.

Canine parvovirus (CPV) is an enteric pathogen that infects, for the most part, dogs, especially puppies. Canine parvovirus infection incurs acute diarrhea, fever, and a low white cell count in dogs and puppies 4 to 5 weeks or more after birth and a cardiomyopathy in younger puppies. If not vaccinated, dogs are highly apt to die of the disease. Vaccines against canine parvovirus may be available, but canine parvovirus is a single-stranded DNA virus with a high mutation rate, and exhibits a significant antigenic modification ability. Thus, immunized prevention against the disease cannot be completely achieved with conventional vaccines.

Because canine parvovirus can be mutated into a variant having new antigenicity, there is a need for a vaccine and a diagnostic test that take account of current canine parvovirus variants by examining genetic compositions of canine parvovirus variants.

The present inventors have made intensive and thorough research into the development of recombinant canine parvovirus 2a VP2 and 2b VP2 antigen proteins as antigenic proteins with excellent antigenicity and immunogenicity. As a consequence, canine parvovirus 2a VP2 and 2b VP2 genes were synthesized after codon optimization, and it was found that the canine parvovirus 2a VP2 or 2b VP2 antigen protein obtained from a transgenic plant modified with a recombinant expression vector comprising the gene exhibits high stability and immunogenicity.

A gene encoding the canine parvovirus 2a VP2 protein may have the nucleotide sequence of SEQ ID NO: 3 or a nucleotide sequence functionally equivalent thereto.

A gene encoding the canine parvovirus 2b VP2 protein may have the nucleotide sequence of SEQ ID NO: 4 or a nucleotide sequence functionally equivalent thereto.

By "functionally equivalent", it is meant that a nucleotide sequence resulting from addition, substitution, or deletion has a sequence homology of 70% or greater, particularly 80% or greater, more particularly 90% or greater, even more particularly 95% or greater to the nucleotide sequence of SEQ ID NO: 3 or 4 and as such, can encode a protein exhibiting substantially the same physiological activity as in that encoded by the nucleotide sequence of SEQ ID NO: 3 or 4. For example, variants that can conduct functionally identical performance to the nucleic acid molecule encoding the canine parvovirus 2a VP2 or 2b VP2 protein although being modified on their some bases by deletion, substitution, or insertion can be included.

In an embodiment of the present disclosure, the recombinant expression vector comprises a polynucleotide, represented by the nucleotide sequence of SEQ ID NO: 1, encoding a RuBisCo transit peptide, a polynucleotide, represented by the nucleotide sequence of SEQ ID NO: 2, encoding 6 consecutive histidine residues; and a gene, represented by the nucleotide sequence of SEQ ID NO: 3, encoding canine parvovirus 2a VP2 protein.

In an embodiment of the present disclosure, the recombinant expression vector includes a polynucleotide, represented by the nucleotide sequence of SEQ ID NO: 1, encoding a RuBisCo transit peptide, a polynucleotide, represented by the nucleotide sequence of SEQ ID NO: 2, encoding 6 consecutive histidine residues; and a gene, represented by the nucleotide sequence of SEQ ID NO: 3, encoding canine parvovirus 2a VP2 protein in that order.

In an embodiment of the present disclosure, the recombinant expression vector comprises a polynucleotide, represented by the nucleotide sequence of SEQ ID NO: 1, encoding a RuBisCo transit peptide, a polynucleotide, represented by the nucleotide sequence of SEQ ID NO: 2, encoding 6 consecutive histidine residues; and a gene, represented by the nucleotide sequence of SEQ ID NO: 4, encoding canine parvovirus 2b VP2 protein.

In an embodiment of the present disclosure, the recombinant expression vector includes a polynucleotide, represented by the nucleotide sequence of SEQ ID NO: 1, encoding a RuBisCo transit peptide, a polynucleotide, represented by the nucleotide sequence of SEQ ID NO: 2, encoding 6 consecutive histidine residues; and a gene, represented by the nucleotide sequence of SEQ ID NO: 4, encoding canine parvovirus 2b VP2 protein in that order.

In an embodiment of the present disclosure, the recombinant expression vector is a recombinant plant expression vector.

According to another aspect thereof, the present disclosure provides a recombinant plant that is transformed with the recombinant expression vector and expresses a canine parvovirus 2a VP2 or 2b VP2 protein.

The plant may belong to the genus *Nicotiana.*

The plant belonging to the genus *Nicotiana* may be *Nicotiana acuminata, Nicotiana africana, Nicotiana alata, Nicotiana attenuata, Nicotiana benthamiana, Nicotiana clevelandii, Nicotiana exigua, Nicotiana glauca, Nicotiana glutinosa* L., *Nicotiana langsdorffii, Nicotiana longiflora, Nicotiana occidentalis, Nicotiana obtusifolia, Nicotiana otophora, Nicotiana plumbaginifolia, Nicotiana quadrivalvis, Nicotiana rustica* L., *Nicotiana suaveolens* Lehm., *Nicotiana sylvestris, Nicotiana tabacum* L., or *Nicotiana tomentosiformis* Good sp., for example, *Nicotiana benthamiana.*

The recombinant plant transformed with a recombinant expression vector comprising a gene encoding canine parvovirus 2a VP2 protein can express canine parvovirus 2a VP2 protein.

In addition, the recombinant plant transformed with a recombinant expression vector comprising a gene encoding canine parvovirus 2b VP2 protein can express canine parvovirus 2b VP2 protein.

The canine parvovirus 2a VP2 and 2b VP2 proteins according to the present disclosure may be advantageously used for diagnosing canine parvovirus infection.

Provided according another embodiment of the present disclosure are a composition and a diagnostic kit for diagnosis of canine parvovirus infection, each comprising the canine parvovirus 2a VP2 or 2b VP2 protein expressed in the transgenic plant.

As used herein, the term "diagnosis" refers to identifying the presence or trait of a pathological condition. In the context of the purpose of the present disclosure, the term "diagnosis" refers to determining the outbreak or risk of canine parvovirus infection.

The diagnostic composition may be prepared using an ordinary method in the art. The diagnostic composition may include a tool, a reagent, etc. generally used for immunological analysis in the art as well as the canine parvovirus 2a VP2 or 2b VP2 antigen protein. Examples of the tool/reagent include a suitable carrier, a marker capable of producing a detectable signal, a solubilizer, a detergent, a buffer, and a stabilizer, but are not limited thereto. When the marker is an enzyme, a substrate and a reaction stopper that can measure enzymatic activity may be included. Within a scope of the suitable carrier, there are soluble carriers, e.g., physiologically acceptable buffers known in the art, such as PBS, and insoluble carriers, e.g., polystyrene, polyethylene, polypropylene, polyester, polyacrylonitrile, a fluorine resin, cross-linked dextran, polysaccharide, a polymer such as magnetic microparticles having metal-coated latex, other paper, glass, metal, agarose, and a combination thereof.

According to another aspect thereof, the present disclosure provides a vaccine composition against canine parvovirus, comprising a canine parvovirus 2a VP2 protein expressed in a transgenic plant transformed with a recombinant expression vector comprising a gene, represented by the nucleotide sequence of SEQ ID NO: 3, encoding canine parvovirus 2a VP2 protein.

Furthermore, the present disclosure provides a vaccine composition against canine parvovirus, comprising a canine parvovirus 2b VP2 protein expressed in a transgenic plant transformed with a recombinant expression vector comprising a gene, represented by the nucleotide sequence of SEQ ID NO: 4, encoding canine parvovirus 2b VP2 protein.

As used herein, the term "vaccine composition" refers to a composition that has a positive influence on the immune response of a subject. The vaccine composition provides a cellular immune response, for example, cytotoxic T lymphocyte-mediated immune response, or a humoral immune response, for example, a systemic or local immune response induced by an antibody.

The vaccine composition may further comprise a pharmaceutically acceptable carrier. So long as it is typically used for formulation, any pharmaceutically acceptable carrier may be contained in the composition of the present disclosure. Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto.

The composition of the present disclosure may further comprise a lubricant, a humectant, a sweetener, a flavorant, an emulsifier, a suspending agent, a preservative, and the like in addition to the above ingredients. For details of suitable pharmaceutically acceptable carriers and preparations, reference may be made to Remington's Pharmaceutical Sciences (19th ed., 1995).

The vaccine composition may comprise other constituents, such as stabilizers, excipients, other pharmaceutically acceptable compounds, or any other antigen or part thereof. The vaccine may be in the form of a lyophilized preparation or as a suspension, all of which are common in the field of vaccine production.

The form of administration for the vaccine composition of the present disclosure may be that of an enteric coated dosage unit, an inoculum for intraperitoneal, intramuscular or subcutaneous administration, an aerosol spray, by oral or intranasal application. Administration in the drinking water or in feed pellets is also possible.

The vaccine composition of the present disclosure may also be transferred as a single vaccine in which immunomodulatory molecules, such as heterologous antigens and cytokines, are expressed in the same recombinant, or may be administered together with an adjuvant. As used herein, the term "adjuvant" generally refers to any material (e.g., alum, Freund's complete adjuvant, Freund's incomplete adjuvant, LPS, poly IC, poly AU, etc.) that increases humoral or cellular immune responses to antigens.

According to another embodiment thereof, the present disclosure provides a method for preventing a canine parvovirus infection, comprising a step of administering a vaccine composition against canine parvovirus infection to a subject, the vaccine composition containing a canine parvovirus 2a VP2 protein expressed in a transgenic plant transformed with a recombinant expression vector comprising a gene, represented by the nucleotide sequence of SEQ ID NO: 3, encoding the canine parvovirus 2a VP2 protein.

In addition, the present disclosure provides a method for preventing a canine parvovirus infection, comprising a step of administering a vaccine composition against canine parvovirus infection to a subject, the vaccine composition containing a canine parvovirus 2b VP2 protein expressed in a transgenic plant transformed with a recombinant expression vector comprising a gene, represented by the nucleotide sequence of SEQ ID NO: 4, encoding the canine parvovirus 2b VP2 protein.

By the term "administration" or "administering", as used herein, it is meant that a prophylactically effective amount of the composition of the present disclosure is directly administered to a subject that suffers from or is at risk of suffering from the above-described diseases, thereby forming an antibody as much in the subject's body.

As used herein, "prophylactically effective amount" refers to an amount sufficient to advantageously provide a prophylactic effect for a subject to be administered the composition.

A suitable dose of the vaccine composition of the present disclosure may vary depending on various factors including a formulating method, a manner of administration, patient's age, body weight, sex, and morbidity, food, a time of administration, a route of administration, an excretion rate, and response sensitivity. An ordinarily skilled veterinarian can easily determine and prescribe an effective dose for prevention. According to a preferable embodiment of the present disclosure, the daily dose of the vaccine composition of the present disclosure is 0.0001-100 mg/kg.

As used herein, the term "prevention" refers to a prophylactic or protective treatment of a disease or a disease condition.

The preventing method of the present disclosure includes a content overlapping with the vaccine composition provided according an aspect of the present disclosure. Hence, the common descriptions therebetween are omitted in order to avoid undue redundancy leading to the complexity of this specification.

Another aspect of the present disclosure contemplates a method for providing information necessary for diagnosis of canine parvovirus infection, comprising a step of detecting a VP2 antibody of canine parvovirus through an antigen-antibody reaction in a sample by using as an antigen a canine parvovirus 2a VP2 protein expressed in a transgenic plant transformed with a recombinant expression vector comprising a gene, represented by the nucleotide sequence of SEQ ID NO: 3, encoding the canine parvovirus 2a VP2 protein.

In addition, the present disclosure also contemplates a method for providing information necessary for diagnosis of canine parvovirus infection, comprising a step of detecting a VP2 antibody of canine parvovirus through an antigen-antibody reaction in a sample by using as an antigen a canine parvovirus 2b VP2 protein expressed in a transgenic plant transformed with a recombinant expression vector comprising a gene, represented by the nucleotide sequence of SEQ ID NO: 4, encoding the canine parvovirus 2b VP2 protein.

The detection of the antigen protein of canine parvovirus may be achieved through an antigen-antibody reaction.

The antigen-antibody reaction may be carried out using at least one selected from the group consisting of histological immunostaining, radioactive immunoassay (RIA), enzyme-linked immunosorbent assay (ELISA), western blotting, immunoprecipitation assay, immunodiffusion assay, complement fixation assay, fluorescence-activated cell sorter (FACS), and protein chip assay, for example, enzyme-linked immunosorbent assay (ELISA).

The sample may be tissues, cells, whole blood, sera, feces, saliva, phlegm, cerebrospinal fluid, or urine from dogs, for example, canine serum.

Advantageous Effects of Invention

The present disclosure provides a recombinant expression vector comprising a gene encoding a canine parvovirus 2a VP2 or 2b VP2 protein, a recombinant plant transformed with the vector, a vaccine composition against canine parvovirus and a diagnostic composition against canine parvovirus infection, each composition comprising the canine parvovirus 2a VP2 protein or 2b VP2 obtained from the recombinant plant. When used, the recombinant plant of the present disclosure can produce the canine parvovirus 2a VP2 or 2b VP2 antigen protein quickly at high efficiency. Employing the recombinant antigen protein, the diagnostic composition for canine parvovirus of the present disclosure is free of the likelihood of contamination with living virus and can allow the quick diagnosis of canine parvovirus infection from tremendous samples with safety.

DETAILED DESCRIPTION

Figure 1:
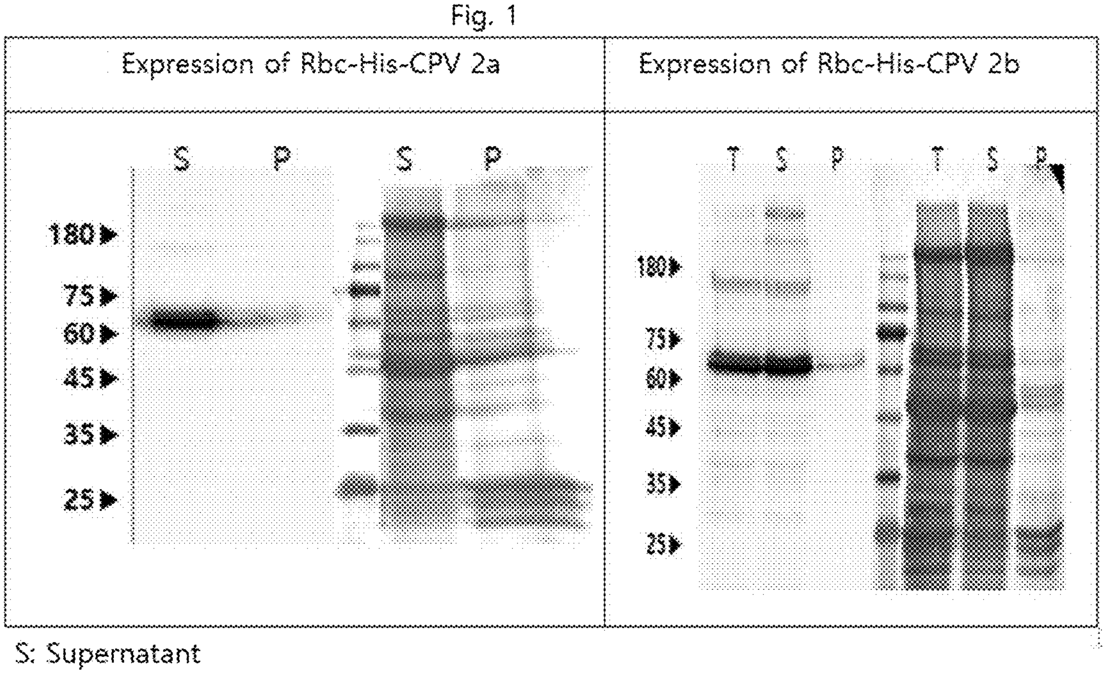
FIG. 1 shows western blot results illustrating recombinant canine parvovirus 2a VP2 and 2b VP2 proteins expressed in *Nicotiana benthamiana.*

A better understanding of the present disclosure may be obtained via the following Examples which are set forth to illustrate, but are not to be construed as limiting the present disclosure.

EXAMPLES

Example 1. Production of Recombinant Canine Parvovirus 2a VP2 and 2b VP2 Proteins

1-1. Preparation of Recombinant Plant Expression Vector Expressing Canine Parvovirus 2a VP2 and 2b VP2 Antigen A canine parvovirus VP2 gene was synthesized in Bioneer Inc. after canine parvovirus 2a VP2 (SEQ ID NO: 5) and 2b VP2 (SEQ ID NO: 6) DNA sequences obtained from canine fecal samples were optimized to fit for *Nicotiana benthamiana* through GenScript's codon optimization program. The optimized polynucleotide sequences of 2a VP2 and 2b VP2 were 1752 bp and 1752 bp long, respectively.

For use in plant expression of canine parvovirus 2a VP2 and 2b VP2 antigens, a recombinant canine parvovirus 2a VP2 or 2b VP2 expression vector was constructed by sequentially linking a polynucleotide encoding RuBisCO transit peptide (SEQ ID NO: 1), a polynucleotide encoding 6 consecutive histidine residues (SEQ ID NO: 2), and a polynucleotide encoding canine parvovirus 2a VP2 protein (SEQ ID NO: 3) or 2b VP2 protein (SEQ ID NO: 4) between the CaMV 35S promoter gene and the NOS terminator in pCAMBIA1300 vector.

1-2. Expression in Recombinant Canine Parvovirus 2a VP2 and 2b VP2 Protein in Plant In order to express recombinant canine parvovirus 2a VP2 and 2b VP2 proteins in a plant, the recombinant expression vector constructed in Example 1 was transformed into *Agrobacterium* GV3101 by electroporation using Gene Pulser Xcell (Bio-Rad, USA) according to the manufacturer's instruction. The transformed GV3101 cells were grown in YEP broth containing suitable antibiotics (yeast extract 10 g, peptone 10 g, NaCl 5 g, kanamycin 50 mg/L, rifampicin 25 mg/L) until they reached a stationary phase. After centrifugation of the cell culture, the pellet was resuspended to 0.5 $OD_{600}$ in an infiltration medium (10 mM Mes, 10 mM MgCl2, 100 mM acetosyringone). The bacterial suspension was incubated for 1 hour at room temperature. Agro-infiltration was carried out by applying the agrobacterial suspension to 4- to 6-week old *Nicotiana benthamiana* leaves at 25° C. through a syringe or vacuum-assisted infiltration.

1-3. Expression

A leaf tissue with a size of about 3 $cm^2$ was homogenized in 100 μl of a homogenization buffer (20 mM Tris-HCl [pH 7.5], 150 mM NaCl, 1 mM EDTA, 1% Triton X-100, 0.1% SDS, 5 mM DTT and plant protease inhibitor cocktail [Sigma-Aldrich]), followed by centrifugation at 20,000×g, 4° C. for 10 min to remove insoluble debris. The sample was separated in 12% SDS-PAGE gel and transferred onto a PVDF membrane (Millipore Merck KGaA of Darmstadt, Germany). Subsequent to a reaction with a monoclonal anti-His antibody (1:1,000 dilution, Invitrogen), detection was made with a chemiluminescent substrate (FIG. 1).

As can be seen in FIG. 1, extensive expression was achieved with the plant expression vector in which a polynucleotide encoding RuBisCO transit peptide, a polynucleotide encoding 6 consecutive histidine residues, and a polynucleotide encoding canine parvovirus 2a VP2 protein or 2b VP2 protein were sequentially linked while poor expression was obtained with a plant expression vector in which the histidine residues were positioned behind the canine parvovirus 2a VP2 protein or 2b VP2 protein.

Example 2. Assay for Immunogenicity of Recombinant Canine Parvovirus 2a VP2 and 2b VP2 Proteins

2-1. Hemagglutination Assay (HA)

Figure 2A:
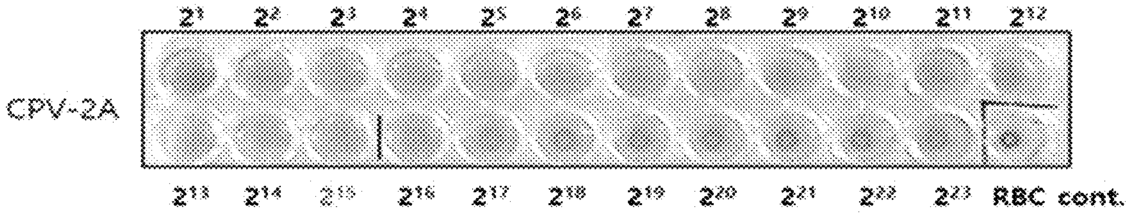
FIG. 2*a* shows hemagglutination assay results for recombinant canine parvovirus 2a VP2 protein expressed in *Nicotiana benthamiana.*
Figure 2B:
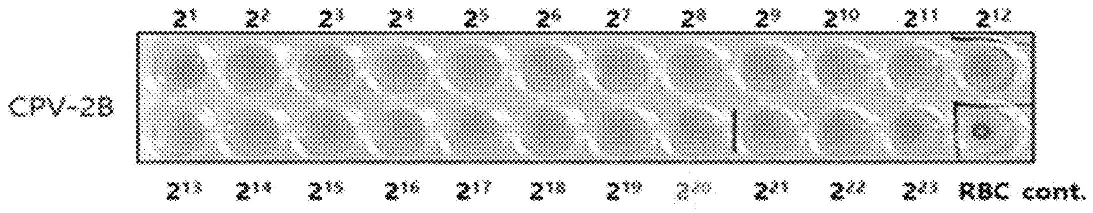
FIG. 2*b* shows hemagglutination assay results for recombinant canine parvovirus 2b VP2 protein expressed in *Nicotiana benthamiana.*

For use HA tests, the recombinant canine parvovirus VP2 proteins were subjected to serial two-fold dilution in 0.6% porcine erythrocytes in Sorensen buffer (pH 6.8). HA titers were expressed as the highest dilution folds which allowed hemagglutination. HA tests were conducted using canine parvovirus 2a VP2 and 2b VP2 proteins expressed in *Nicotiana benthamiana*. As a test result, HA titers were measured to be $2^{15}$ HA units for canine parvovirus 2a VP2 protein and $2^{20}$ HA units for canine parvovirus 2b VP2 protein (FIGS. 2*a* and 2*b*).

2-2. Immunogenicity Evaluation

Healthy female guinea pigs free of canine parvovirus-specific antibodies were divided into groups of three. The groups were immunized with the canine parvovirus 2a VP2 or 2b VP2 protein mixed with adjuvant A, a canine parvovirus inactivated vaccine, and PBS, respectively. As an immunogen, 100 μl of the recombinant canine parvovirus 2a VP2 or 2b VP2 protein (pertinent HA titer 1:$2^8$) was intramuscularly injected into guinea pigs, followed by two rounds of boosting at intervals of two weeks. On day 28 after primary immunization, a blood sample was taken and coagulated at 37° C. for 2 hours. Sera were taken and inactivated at 56° C. for 30 min. HI was used for analyzing canine parvovirus-specific antibodies. After being mixed at 1:1 ratio with 25% kaolin solution, stirred for 1 hour, and mixed at 1:1 ratio with 50% pig blood corpuscle solution, the sera were separated to remove non-specific antibodies. The sera were subjected to serial two-fold dilution. The dilutions were reacted at 4° C. for 1 hour with a 1:1 dilution of the canine parvovirus 2a VP2 or 2b VP2 protein, expressed in *Nicotiana benthamiana*, having 8 HA units after back titration. Subsequently, 0.6% porcine blood corpuscle was 1:1 diluted and reacted at 4° C. for 2 hours before measurement.

Figure 3A:
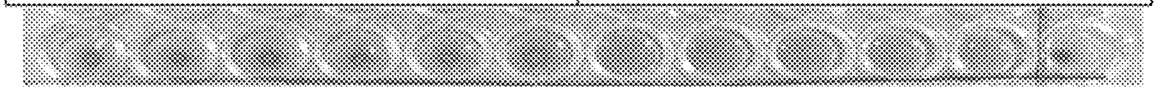
FIG. 3*a* shows hemagglutination inhibition (HI) titer test results in guinea pigs immunized with the recombinant canine parvovirus 2a VP2 protein expressed in *Nicotiana benthamiana.*

As a result, a HI titer of $2^6$ was detected in two guinea pigs injected with the canine parvovirus 2a VP2 protein expressed in the plant (FIG. 3*a*).

Figure 3B:
FIG. 3*b* shows hemagglutination inhibition (HI) titer test results in guinea pigs immunized with the recombinant canine parvovirus 2b VP2 protein expressed in *Nicotiana benthamiana.*

Two guinea pigs injected with the canine parvovirus 2b VP2 protein expressed in the plant were measured to have a HI titer of $2^8$ (FIG. 3*b*).

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A recombinant expression vector comprising:

i) a polynucleotide encoding RuBisCo transit peptide, 6 consecutive histidine residues, and canine parvovirus 2a VP2 protein, wherein the polynucleotide consists of the nucleotide sequences of SEQ ID NOS: 1 to 3 sequentially; or ii) a polynucleotide encoding RuBisCo transit peptide, 6 consecutive histidine residues, and canine parvovirus 2b VP2 protein, wherein the polynucleotide consists of the nucleotide sequences of SEQ ID NOS: 1, 2, and 4 sequentially.

2. A recombinant plant, wherein the recombinant plant is transformed with the recombinant expression vector of claim 1.

* * * * *